US010372876B2

(12) United States Patent
Kopylov

(10) Patent No.: US 10,372,876 B2
(45) Date of Patent: Aug. 6, 2019

(54) SYSTEM AND METHOD FOR PROVIDING BREAST IMAGE DATA

(71) Applicant: Agfa HealthCare Inc., Mississauga (CA)

(72) Inventor: Viktor Kopylov, Waterloo (CA)

(73) Assignee: AGFA HEALTHCARE INC., Mississauga (CA)

( * ) Notice: Subject to any disclaimer, the term of this patent is extended or adjusted under 35 U.S.C. 154(b) by 24 days.

(21) Appl. No.: 15/411,373

(22) Filed: Jan. 20, 2017

(65) Prior Publication Data
US 2018/0211004 A1 Jul. 26, 2018

(51) Int. Cl.
G06K 9/20 (2006.01)
G06T 3/40 (2006.01)
G06F 19/00 (2018.01)

(52) U.S. Cl.
CPC ......... *G06F 19/321* (2013.01); *G06K 9/2054* (2013.01); *G06T 3/4092* (2013.01)

(58) Field of Classification Search
None
See application file for complete search history.

(56) References Cited

U.S. PATENT DOCUMENTS

| 5,671,350 | A | | 9/1997 | Wood | |
|---|---|---|---|---|---|
| 5,776,062 | A | * | 7/1998 | Nields | A61B 6/0435 128/915 |
| 6,022,362 | A | * | 2/2000 | Lee | A61B 10/0266 600/564 |
| 6,459,925 | B1 | * | 10/2002 | Nields | A61B 6/0435 128/915 |

(Continued)

FOREIGN PATENT DOCUMENTS

| CN | 1216202 A | 5/1999 |
|---|---|---|
| CN | 1273516 A | 11/2000 |

(Continued)

OTHER PUBLICATIONS

Hong et al., "Segmentation of Regions of Interest in Mammograms in a Topographic Approach", IEEE Transactions on Information Technology in Biomedicine, IEEE Service Center, Los Alamitos, CA, U.S., vol. 13, No. 1, Jan. 1, 2010, pp. 129-139, XP011296552, ISSN: 1089-7771, Abstract—p. 132, right-hand column, lines 18-20 and p. 135, left-hand column, lines 52-55.

(Continued)

*Primary Examiner* — Kevin Ky
(74) *Attorney, Agent, or Firm* — Bereskin & Parr LLP/S.E.N.C.R.L., s.r.l.; Isis E. Caulder; T. Cameron Gale

(57) ABSTRACT

A system and method for providing breast image data. A transmission request is transmitted from a workstation to an imaging server with identifying characteristics for a mammography image. A pre-determined breast window for the mammography image is identified. An unprocessed image stored on the server that corresponds to the mammography image is identified, and breast image data can be determined for unprocessed image. The breast image data includes a breast window image that can be determined by applying the pre-determined breast window to the unprocessed image. The breast image data is transmitted to the clinician workstation, and the breast window image is displayed at the clinician workstation.

18 Claims, 4 Drawing Sheets

(56) References Cited

U.S. PATENT DOCUMENTS

| | | |
|---|---|---|
| 6,460,123 B1 | 10/2002 | Blumenau |
| 6,502,105 B1 | 12/2002 | Yan et al. |
| 6,529,757 B1 | 3/2003 | Patel et al. |
| 6,564,225 B1 | 5/2003 | Brogliatti et al. |
| 6,574,629 B1 | 6/2003 | Cooke, Jr. et al. |
| 6,629,110 B2 | 9/2003 | Cane et al. |
| 6,799,206 B1 | 9/2004 | Workman et al. |
| 6,990,239 B1 | 1/2006 | Nelson |
| 7,058,853 B1 | 6/2006 | Kavanappillil et al. |
| 7,076,578 B2 | 7/2006 | Poisner et al. |
| 7,129,961 B1 | 10/2006 | Samra |
| 7,142,633 B2 | 11/2006 | Eberhard et al. |
| 7,599,542 B2 | 10/2009 | Brockway et al. |
| 7,764,820 B2 | 7/2010 | Wu et al. |
| 7,844,571 B2 | 11/2010 | König |
| 7,865,002 B2 | 1/2011 | Basilico et al. |
| 7,885,443 B2 | 2/2011 | Zingaretti et al. |
| 7,970,203 B2 | 6/2011 | Avinash et al. |
| 7,992,100 B2 | 8/2011 | Lundström et al. |
| 8,005,921 B2 | 8/2011 | Ho et al. |
| 8,044,972 B2 | 10/2011 | Häll et al. |
| 8,051,386 B2 | 11/2011 | Rosander et al. |
| 8,194,947 B2 | 6/2012 | Zingaretti et al. |
| 8,453,154 B2 | 5/2013 | Mir et al. |
| 8,571,280 B2 | 10/2013 | Mathew |
| 8,649,578 B2 | 2/2014 | Yang |
| 8,923,594 B2 | 12/2014 | Wehnes et al. |
| 9,020,304 B2 | 4/2015 | Dorn et al. |
| 9,474,497 B2 | 10/2016 | Kopylov |
| 2002/0052884 A1 | 5/2002 | Farber et al. |
| 2002/0056634 A1 | 5/2002 | Pitts, Jr. et al. |
| 2002/0077648 A1* | 6/2002 | Lee ............... A61B 10/0266 606/170 |
| 2002/0087588 A1 | 7/2002 | McBride et al. |
| 2002/0152231 A1 | 10/2002 | Silva-Craig et al. |
| 2003/0158481 A1* | 8/2003 | Stotzka ............ A61B 8/0825 600/437 |
| 2004/0015373 A1 | 1/2004 | Silva-Craig et al. |
| 2005/0235122 A1 | 10/2005 | Pillai et al. |
| 2006/0005048 A1 | 1/2006 | Osaki et al. |
| 2006/0098855 A1 | 5/2006 | Gkanatsios et al. |
| 2006/0147101 A1 | 7/2006 | Zhang et al. |
| 2006/0171573 A1 | 8/2006 | Rogers |
| 2006/0212317 A1* | 9/2006 | Hahn ................ G06F 19/321 705/3 |
| 2006/0228015 A1 | 10/2006 | Brockway et al. |
| 2007/0122021 A1* | 5/2007 | Zingaretti ........... G06T 7/0014 382/132 |
| 2008/0031504 A1 | 2/2008 | Worrell |
| 2009/0086891 A1* | 4/2009 | Ofuji ..................... A61B 6/463 378/37 |
| 2009/0141955 A1* | 6/2009 | Morita ................ G06T 7/0012 382/128 |
| 2010/0122204 A1 | 5/2010 | Sonnemans |
| 2010/0128950 A1 | 5/2010 | Woods et al. |
| 2011/0109650 A1 | 5/2011 | Kreeger et al. |
| 2011/0216949 A1* | 9/2011 | Yang ..................... G06T 7/11 382/128 |
| 2012/0053446 A1* | 3/2012 | Lossev ................ G06T 7/0012 600/407 |
| 2013/0103647 A1 | 4/2013 | Ho et al. |
| 2015/0010219 A1* | 1/2015 | Behiels ................ G06T 7/12 382/128 |
| 2015/0199790 A1* | 7/2015 | Kopylov .............. A61B 6/502 345/660 |
| 2015/0356757 A1* | 12/2015 | Marshall ............. G06T 11/006 382/131 |

FOREIGN PATENT DOCUMENTS

| | | |
|---|---|---|
| CN | 1416095 A | 5/2003 |
| CN | 101014052 B | 11/2011 |
| CN | 102947841 A | 2/2013 |
| CN | 105916435 A | 8/2016 |
| EP | 1 783 611 B1 | 6/2009 |
| EP | 2 372 649 B1 | 10/2012 |
| EP | 2 629 263 A1 | 8/2013 |
| JP | 2003-316626 A | 11/2003 |
| WO | 2011/044295 A3 | 4/2011 |
| WO | 2015/106339 A1 | 7/2015 |

OTHER PUBLICATIONS

International Search Report and Written Opinion dated Apr. 12, 2018 in corresponding International Patent Application No. PCT/CA2018/050035.

"Digital Imaging and Communications in Medicine (DICOM) Part 1: Introduction and Overview", 2004, National Electrical Manufacturers Association, Rosslyn Virginia, U.S.A., pp. 1-21.

"Digital Imaging and Communications in Medicine (DICOM) Part 4: Service Class Specifications", 2004, National Electrical Manufacturers Association, Rosslyn Virginia, U.S.A., pp. 1-342.

* cited by examiner

SYSTEM AND METHOD FOR PROVIDING BREAST IMAGE DATA

FIELD

The embodiments described herein relate to systems and methods for managing medical data, and in particular systems and methods for managing breast image data.

BACKGROUND

Medical imaging can be used as a clinical and diagnostic tool for assessing patients. Medical imaging techniques can reveal internal structures of a patient's body, often with minimal intrusion. The medical images generated can be used to diagnose and treat diseases, such as by identifying the presence of cancer in a patient. For example, mammography images of a patient's breast are frequently used to assess whether an individual is likely to have breast cancer.

Diagnosing the presence of diseases such as cancer can be difficult because individual physiology can vary from patient to patient. To identify changes in a patient's physiology, clinicians may compare images acquired from that patient over time. Comparing images acquired at different time may help a clinician recognize changes in a patient's physiology and assess whether a disease is present. This may assist the clinician in accurately diagnosing a patient's condition. This may also allow the clinician to monitor the efficacy of a treatment regime, and determine the proper course of treatment.

As medical imaging data increases in quality and resolution, the data size of medical imaging files increases. These files are often stored in centralized databases or remote archives that are accessible over a network. When a clinician is interested in reviewing past medical images, the medical imaging data is typically retrieved from the remote storage database and transmitted to a clinician workstation. As the size of medical images increases, the bandwidth required to transmit these images also increases. This can slow or delay a clinician's ability to review images, particularly if multiple images are to be reviewed such as a volume-based image series. Similarly, where a clinician screens a large number of patients using medical imaging data, this may reduce the number of patients they can assess each day.

SUMMARY

In accordance with an aspect of an embodiment of the invention, there is provided a method for providing breast image data. The method can include receiving from a clinician workstation, at a medical imaging database, a transmission request for breast image data, the transmission request including identifying characteristics for a particular mammography image; identifying at least one unprocessed mammography image stored by the medical imaging database that corresponds to the particular mammography image using the identifying characteristics; identifying a pre-determined breast window for the particular mammography image, the pre-determined breast window being defined by processed mammography data of a processed mammography image that corresponds to the particular mammography image; determining, for each of the at least one unprocessed mammography images, breast image data stored in the medical imaging database, the breast image data including a breast window image determined by applying the pre-determined breast window defined by the processed mammography data to that unprocessed mammography image; transmitting the breast image data from the medical imaging database to the clinician workstation; and displaying at the clinician workstation the breast window image for each of the at least one unprocessed mammography images received from the medical imaging database.

In some embodiments, each of the at least one unprocessed mammography images comprises a breast window region and a secondary region, and the method may further include determining the breast image data for each of the at least one unprocessed mammography images by applying the pre-determined breast window to that unprocessed mammography image; and the breast image data transmitted from the medical imaging database to the clinician workstation includes image data corresponding to the breast window region and excludes image data corresponding to at least a portion of the secondary region.

In some embodiments, the method may further include receiving a subsequent transmission request for additional breast image data at the medical imaging database from the clinician workstation, the subsequent transmission request identifying a particular unprocessed mammography image of the at least one unprocessed mammography image; and transmitting additional breast image data for the particular unprocessed mammography image from the medical imaging database to the clinician workstation, wherein the additional breast image data comprises an additional portion of the secondary region that was excluded from the breast image data previously transmitted.

In some embodiments, the identifying characteristics in the transmission request from the clinician workstation include the processed mammography data defining the pre-determined breast window.

In some embodiments, a current mammography image is stored at the clinician workstation and the method can further include generating the processed mammography data by processing the current mammography image at the clinician workstation to identify the pre-determined breast window.

In some embodiments, the method may further include storing the pre-determined breast window at the medical imaging database in association with the identifying characteristics for the mammography image.

In some embodiments, the method may further include identifying a plurality of initial mammography images corresponding to the particular mammography image at the medical imaging database, the plurality of initial mammography images including the at least one unprocessed mammography image; identifying the processed mammography image in the plurality of initial mammography images; and identifying the processed mammography data of the processed mammography image at the medical imaging database to identify the pre-determined breast window.

In some embodiments, the at least one unprocessed mammography image comprises a plurality of unprocessed mammography images corresponding to the particular mammography image acquired at different times.

In some embodiments, the particular mammography image belongs to an image series including a plurality of related mammography images and the method can further include, for each related mammography image of that image series: identifying the at least one unprocessed mammography image stored in the medical imaging database that corresponds to that related mammography image using the identifying characteristics; identifying the pre-determined breast window for that related mammography image, the pre-determined breast window being defined by processed mammography data of the processed mammography image that corresponds to that related mammography image; determining, for each of the at least one unprocessed mammography images, breast image data stored in the medical imaging database, the breast image data including the breast window image determined by applying the pre-determined breast window defined by the processed mammography data to that unprocessed mammography image; and transmitting the breast image data from the medical imaging database to the clinician workstation.

In some embodiments, the method may further include identifying a scaling factor for a particular unprocessed mammography image, the scaling factor determined based on a scaling relationship between the particular unprocessed mammography image and the processed mammography image; and adjusting the particular unprocessed mammography image using the scaling factor prior to applying the pre-determined breast window to the particular unprocessed mammography image.

In accordance with an embodiment of the invention, there is provided a system for providing breast image data. The system can include a medical imaging server with a server processor and a medical imaging database; and a clinician workstation in communication with the medical imaging server, the clinician workstation having a processor, a memory and a display device. The server processor can be configured to receive a transmission request for breast image data from the clinician workstation, the transmission request including identifying characteristics for a particular mammography image; identify at least one unprocessed mammography image stored in the medical imaging database that corresponds to the particular mammography image using the identifying characteristics; determine, for each of the at least one unprocessed mammography images, breast image data stored in the medical imaging database, the breast image data including a breast window image determined by applying a pre-determined breast window to that unprocessed mammography image; and transmit the breast image data from the medical imaging database to the clinician workstation. The processor of the clinician workstation can be configured to receive the breast image data from the medical imaging database to the clinician workstation; and display the breast window image for each of the at least one unprocessed mammography images received from the medical imaging database on the display device. The pre-determined breast window is defined by processed mammography data of a processed mammography image that corresponds to the mammography image.

In some embodiments, each of the at least one unprocessed mammography images comprises a breast window region and a secondary region; the server processor can be further configured to determine the breast image data for each of the at least one unprocessed mammography images by applying the pre-determined breast window to that unprocessed mammography image; and the breast image data transmitted from the medical imaging database to the clinician workstation includes image data corresponding to the breast window region and excludes image data corresponding at least a portion of the secondary region.

In some embodiments, the server processor can be further configured to receive a subsequent transmission request for additional breast image data from the clinician workstation, the subsequent transmission request identifying a particular unprocessed mammography image of the at least one unprocessed mammography image; and transmit the additional breast image data for the particular unprocessed mammography from the medical imaging database to the clinician workstation, wherein the additional breast image data comprises an additional portion of the secondary region that was excluded from the breast image data previously transmitted.

In some embodiments, the identifying characteristics in the transmission request from the clinician workstation include the processed mammography data defining the pre-determined breast window.

In some embodiments, the processor of the clinician workstation can be further configured to store a current mammography image in the memory of the clinician workstation; and generate the processed mammography data by processing the current mammography image to identify the pre-determined breast window.

In some embodiments, the server processor can be further configured to store the pre-determined breast window in the medical imaging database in association with the identifying characteristics for the particular mammography image.

In some embodiments, the server processor can be further configured to identify a plurality of initial mammography images corresponding to the particular mammography image on the medical imaging database, the plurality of initial mammography images including the at least one unprocessed mammography image; identify the processed mammography image in the plurality of initial mammography images; and identify the processed mammography data from the processed mammography image at the medical imaging database to identify the pre-determined breast window.

In some embodiments, the at least one unprocessed mammography image comprises a plurality of unprocessed mammography image corresponding to the particular mammography image acquired at different times.

In some embodiments, the particular mammography image belongs to an image series including a plurality of related mammography images and the server processor can be configured to, for each related mammography image of that image series, identify the at least one unprocessed mammography image stored in the medical imaging database that corresponds to that related mammography image using the identifying characteristics; identify the pre-determined breast window for that related mammography image, the pre-determined breast window being defined by processed mammography data of the processed mammography image that corresponds to that related mammography image; determine, for each of the at least one unprocessed mammography images, breast image data stored in the medical imaging database, the breast image data including the breast window image determined by applying the pre-determined breast window defined by the processed mammography data to that unprocessed mammography image; and transmit the breast image data from the medical imaging database to the clinician workstation.

In some embodiments, the server processor can be further configured to identify a scaling factor for a particular unprocessed mammography image, the scaling factor determined based on a scaling relationship between the particular unprocessed mammography image and the processed mammography image; and adjust the particular unprocessed mammography image using the scaling factor prior to applying the pre-determined breast window to the particular unprocessed mammography image.

Further aspects and advantages of the embodiments described herein will appear from the following description taken together with the accompanying drawings.

DRAWINGS

For a better understanding of the embodiments described herein and to show more clearly how they may be carried into effect, reference will now be made, by way of example only, to the accompanying drawings which show at least one exemplary embodiment, and in which.

Figure 1:
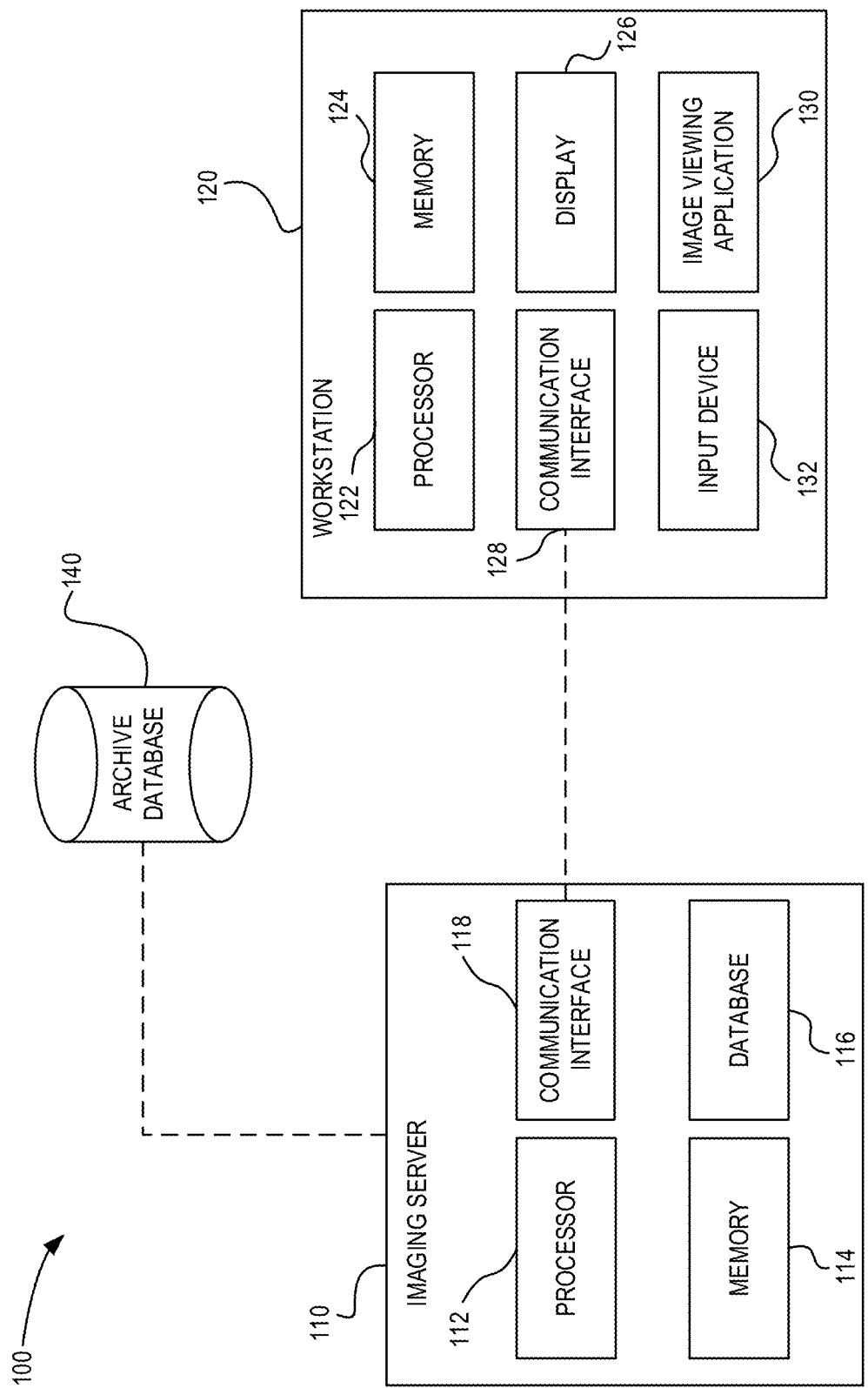
FIG. 1 is a block diagram of a system for providing medical imaging data.

The skilled person in the art will understand that the drawings, described below, are for illustration purposes only. The drawings are not intended to limit the scope of the applicants' teachings in any way. Also, it will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DESCRIPTION OF VARIOUS EMBODIMENTS

It will be appreciated that numerous specific details are set forth in order to provide a thorough understanding of the exemplary embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description and the drawings are not to be considered as limiting the scope of the embodiments described herein in any way, but rather as merely describing the implementation of the various embodiments described herein. Where considered appropriate, for simplicity and clarity of illustration, reference numerals may be repeated among the figures to indicate corresponding or analogous elements or steps.

The embodiments of the systems and methods described herein may be implemented in hardware or software, or a combination of both. However, preferably, these embodiments are implemented in computer programs executing on programmable computers each comprising at least one module component which comprises at least one processor (e.g. a microprocessor), a data storage system (including volatile and non-volatile memory and/or storage elements), at least one input device, and at least one output device. For example and without limitation, the programmable computers (referred to below as computing devices) may be a personal computer, laptop, personal data assistant, and cellular telephone, smart-phone device, tablet computer, and/or wireless device. Program code is applied to input data to perform the functions described herein and generate output information. The output information is applied to one or more output devices, in known fashion.

Each program is preferably implemented in a high level procedural or object oriented programming and/or scripting language to communicate with a computer system. However, the programs can be implemented in assembly or machine language, if desired. In any case, the language may be a compiled or interpreted language. Each such computer program is preferably stored on a storage media or a device (e.g. ROM or magnetic diskette) readable by a general or special purpose programmable computer, for configuring and operating the computer when the storage media or device is read by the computer to perform the procedures described herein. The subject system may also be considered to be implemented as a computer-readable storage medium, configured with a computer program, where the storage medium so configured causes a computer to operate in a specific and predefined manner to perform the functions described herein.

Furthermore, the system, processes and methods of the described embodiments are capable of being distributed in a computer program product comprising a computer readable medium that bears computer usable instructions for one or more processors. The medium may be provided in various forms, including one or more diskettes, compact disks, tapes, chips, wireline transmissions, satellite transmissions, internet transmission or downloadings, magnetic and electronic storage media, digital and analog signals, and the like. The computer useable instructions may also be in various forms, including compiled and non-compiled code.

The terms "an embodiment," "embodiment," "embodiments," "the embodiment," "the embodiments," "one or more embodiments," "some embodiments," and "one embodiment" mean "one or more (but not all) embodiments of the present invention(s)," unless expressly specified otherwise.

The terms "including," "comprising" and variations thereof mean "including but not limited to," unless expressly specified otherwise. A listing of items does not imply that any or all of the items are mutually exclusive, unless expressly specified otherwise. The terms "a," "an" and "the" mean "one or more," unless expressly specified otherwise.

Further, although process steps, method steps, algorithms or the like may be described (in the disclosure and/or in the claims) in a sequential order, such processes, methods and algorithms may be configured to work in alternate orders. In other words, any sequence or order of steps that may be described does not necessarily indicate a requirement that the steps be performed in that order. The steps of processes described herein may be performed in any order that is practical. Further, some steps may be performed simultaneously.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article.

The embodiments described herein provide systems, methods and computer program products for providing and displaying medical imaging data. In particular, the embodiments described herein may provide systems, methods and computer program products for transmitting and displaying breast image data.

Breast image data such as a mammography image is frequently used in clinical assessments to diagnose whether an individual has breast cancer. A mammography image may be part of a series of mammography images captured from an individual's breast, such as a volume-based series of mammography images. A clinician may review the mammography images to attempt to identify whether cancer is present in an individual's breast.

When examining breast image data, clinicians may compare mammography images of the same breast (typically captured from the same perspective) from different times, e.g. images captured over a period of months or years. For instance, a clinician may compare a mammography image captured during a recent imaging session, with mammography images captured during one or more preceding imaging sessions. This may allow the clinician to identify changes in an individual's breast images over time to facilitate a diagnosis.

Clinician workstations may have storage limitations that prevent them from storing the medical imaging data a clinician is likely to view over the course of a day, or even for an individual patient. Additionally, medical imaging data is often captured over a period of time and from different imaging locations (e.g. different hospitals). In order to compare current mammography images with previously acquired images, or more generally to compare mammography images acquired at different times, clinicians may need to access medical image data that is stored remotely.

Medical imaging data is often stored in databases or electronic medical records that are remote from the computers/workstations used by clinicians when evaluating patients. These databases may include mammography images that are unprocessed to do not include data indicating regions of interest such as a breast window. For instance, mammography images generated from legacy systems or digitized versions of non-digital mammography images may be stored in a patient's electronic medical records. These unprocessed images may need to be manually reviewed or processed to identify the relevant image portions that a clinician is interested in reviewing.

Transmitting mammography images from a remote database to a clinician workstation may delay the ability of a clinician to assess a patient. As medical images increase in resolution, the corresponding medical imaging data increases in size and in turn the bandwidth required to transmit images also increases. As well, when a clinician is interested in reviewing multiple mammography images (e.g. images from multiple different acquisition times, multiple images from an image series), this delay may be increased. This can result in increased network latency, and may delay a clinician's ability to assess a patient.

Embodiments of the systems and methods described herein may reduce bandwidth requirements for transmitting breast image data to a clinician. The embodiments described herein may similarly increase the delivery speed for transmitting relevant breast image data to the clinician. Embodiments described herein may use a breast window that is determined for a particular mammography image and apply that breast window to a corresponding unprocessed mammography image. By applying this pre-determined breast window to an unprocessed mammography image, a breast window image can be determined. In some cases, rather than transmitting the entire mammography image for review by a clinician, the breast window image generated from the unprocessed mammography image may be transmitted while excluding some of the background of the image. This may reduce the data size of the image being transmitted while still providing a clinician with a high resolution image of the portion of the mammography image needed to assess the patient.

A transmission request for breast image data may be received at a medical imaging server. The transmission request may include identifying characteristics of a particular mammography image a clinician is interested in reviewing. For example, the clinician may be reviewing a current mammography image and may be interested in comparing that current mammography image with previously acquired images of the same breast. The identifying characteristics may identify characteristics of the current mammography image that allow corresponding mammography images stored in the medical imaging database to be identified. In general, the corresponding mammography images will be the same mammography image of the patient captured at a different time.

In some cases, the corresponding mammography images stored in the medical imaging database will include at least one unprocessed mammography image. The at least one unprocessed mammography image may include one or more unprocessed mammography images acquired at different times. An unprocessed mammography image as used herein generally refers to a mammography image for which a breast window region (i.e. a region enclosing breast tissue) has not been identified. Breast image data for the unprocessed mammography image can then be determined and transmitted to the clinician workstation for review by a clinician. The breast image data generally includes a breast window image that includes breast tissue shown in the mammography image. The breast window image for the unprocessed mammography image can be identified by applying a pre-determined breast window that corresponds to the particular mammography image.

The breast window image may be determined at the medical imaging database prior to transmitting the breast image data to the clinician workstation. Thus, the breast image data transmitted can be determined to include the breast window image and exclude other background regions that may be less relevant to the clinician. This may reduce the image data size of the breast image data being transmitted.

A pre-determined breast window corresponding to the particular mammography image can be determined from processed mammography data of a processed mammography image that corresponds to the particular mammography image. For instance, the pre-determined breast window may be determined by processing the current mammography image at the clinician workstation. An example of method for defining a breast window in a mammography image is described in U.S. Pat. No. 8,649,578 to Yang, the entirety of which is incorporated herein by reference. The pre-determined breast window may then be included with the identifying characteristics sent in the transmission request.

In some cases, the particular mammography image may one image from among a mammography image series. In such cases, a pre-determined breast window for each particular mammography image in the mammography image series may be determined using methods described in U.S. patent application Ser. No. 14/155,851, published as US2015/0199790A1 to Kopylov the entirety of which is incorporated herein by reference in its entirety.

The pre-determined breast window may also be determined from a processed mammography image stored in the medical imaging database. For example, one of the corresponding mammography images stored on the medical imaging database may include processed mammography data defining the pre-determined breast window while a second corresponding mammography image may be unprocessed. The pre-determined breast window from that processed mammography image may then be applied to the unprocessed mammography image.

The unprocessed mammography images stored on the medical imaging database will typically include a breast region that includes breast tissue and a secondary region that does not include breast tissue. A region surrounding the breast tissue, such as a breast window region may be defined that includes all the breast tissue while including a minimal amount of the secondary region. For example, the breast window region may be defined to include all the breast tissue points and then only such portion of the secondary region that the image is formatted to the display screen for a clinician. By applying a pre-determined breast window to the unprocessed mammography image, the breast window region may be extracted and transmitted to the clinician workstation while excluding the remainder of the secondary region.

This breast window image may then be displayed at the clinician workstation. As the breast window image will typically include all, or substantially all, the breast tissue points from a mammography image, the breast window image may provide sufficient data to allow the clinician to assess a patient.

In some embodiments, the breast window image may be extracted from an unprocessed mammography image in response to receiving the transmission request. The medical imaging database may store breast image data using a breast window buffer and a remainder buffer. The breast window buffer can store breast window images extracted from each corresponding mammography image. The remainder buffer can store one or more remainder images of each mammography image with the breast window image extracted. The remainder images generally include background regions from the mammography image that may be excluded from a breast window image. When a transmission request is received at the medical imaging database, relevant breast window images in the breast window buffer can be identified and transmitted to the clinician workstation.

In some embodiments, a remainder image may subsequently be transmitted to the clinician workstation. A subsequent or remainder transmission request may be received at the medical imaging database from the clinician workstation. The remainder image may then be transmitted in response to the remainder transmission request. In some embodiments, a remainder image may be transmitted when a server processor at the medical imaging database identifies sufficient available network bandwidth, e.g. a system idle condition.

In general, each breast window image and remainder image may be compressed prior to transmission to the clinician workstation. The received breast window images and remainder images can be decompressed at the clinician workstation.

In some embodiments, the clinician workstation may store breast image data locally in a workstation memory. The stored breast image data can include breast window images and remainder images received from the database processor. After transmitting a request for new breast image data, a workstation processor may determine that insufficient storage space is available in the workstation memory. The workstation processor may then determine if any remainder images are stored in the workstation memory, and release at least one identified remainder image from the workstation memory. In some embodiments, the workstation processor may release breast window images from the workstation memory if and only if no remainder images are stored in the workstation memory. Since, at first, a clinician may only need to see the breast window image, embodiments described herein may deliver a breast window sub-image first and only then, if elected, a remainder image to review.

The disclosed embodiments may facilitate a clinician's access to remote images by reducing network bandwidth and latency. For each transmission request, the amount of data that needs to be transmitted to provide the clinician with a suitable mammography image to read/review and diagnose may be reduced. In turn, the image may be delivered more rapidly as less data needs to be transmitted and may facilitate end user experience as the image is delivered with relevant image regions while excluding regions likely to be irrelevant. Similarly, the number of images that may be stored locally on the clinician workstation may be increased if only breast window images are transmitted. This may facilitate ongoing delivery of subsequent breast window images while a clinician is reviewing a particular breast window image.

Referring now to FIG. 1, shown therein is a block diagram of a system 100 for providing breast image data. System 100 includes an imaging server 110, a workstation 120 and an archive database 140. The workstation 120, imaging server 110 and archive database 140 can be coupled over a network, such as the Internet.

The network may be constructed from one or more computer network technologies, such as IEEE 802.3 (Ethernet), IEEE 802.11 and similar technologies. Typically, the connections between workstation 120, imaging server 110 and archive database 140 and the Internet may be made via a firewall server (not shown).

Computers and computing devices such as workstation 120, imaging server 110 and archive database 140 may be connected to the network or a portion thereof via suitable network interfaces. In some cases, the workstation 120 and imaging server 110 may be located remotely from one another and the workstation 120 may connect to imaging server 110 via the Internet and/or using networks such as a telecommunications network. In other cases, the workstation 120 may be directly linked to imaging server 110, for example, via a Universal Serial Bus, Bluetooth™ or Ethernet connection.

The clinician device or workstation 120 may be a computer such as a smart phone, desktop or laptop computer, which can connect to a network via a wired Ethernet connection or a wireless connection. The workstation 120 has a processor 122, a memory 124 that may include volatile memory and non-volatile storage, at least one communication interface 128, input devices 132 such as a keyboard and trackpad, output devices such as a display device 126 and speakers, and various other input/output devices as will be appreciated. The workstation 120 may also include computing devices such as a smartphone or tablet computer.

Processor 122 is a computer processor, such as a general purpose microprocessor. In some other cases, processor 122 may be a field programmable gate array, application specific integrated circuit, microcontroller, or other suitable computer processor.

Processor 122 is coupled to display device 126, which is a suitable display for outputting information and data as needed by various computer programs. In particular, display device 126 may display graphical user interfaces (GUI), such as the example user interfaces shown in FIGS. 4A-4C discussed below. The clinician device 120 may execute an operating system, such as Apple iOS™, Microsoft Windows™, GNU/Linux, or other suitable operating system.

Communication interface 128 is one or more data network interface, such as an IEEE 802.3 or IEEE 802.11 interface, for communication over a network.

Processor 122 is coupled, via a computer data bus, to memory 124. Memory 124 may include both volatile and non-volatile memory. Non-volatile memory stores computer programs consisting of computer-executable instructions, which may be loaded into volatile memory for execution by processor 122 as needed. It will be understood by those of skill in the art that references herein to workstation 120 as carrying out a function or acting in a particular way imply that processor 122 is executing instructions (e.g., a software program/application) stored in memory 124 and possibly transmitting or receiving inputs and outputs via one or more interface. Memory 124 may also store data input to, or output from, processor 122 in the course of executing the computer-executable instructions.

The imaging server 110 may be a computer such as a desktop or server computer, which can connect to a network via a wired Ethernet connection or a wireless connection. The imaging server 110 has a processor 112, a memory 114 that may include volatile memory and non-volatile storage, at least one communication interface 118, and a medical imaging database 116. The processor 112, memory 114, and communication interface 118 may be implemented in generally the same manner as with processor 122, memory 124, and communication interface 128 respectively.

Although shown as separate elements, it will be understood that database 116 may be stored in memory 114. Optionally, imaging server 110 may include additional input or output devices, although this is not required. As with all devices shown in system 100, there may be multiple servers 110, although not all are shown. In some cases, server 110 may be distributed over a plurality of computing devices, for instance operating as a cloud server. As with clinician device 120, references to acts or functions by imaging server 110 imply that processor 112 is executing computer-executable instructions (e.g., a software program) stored in memory 114.

As noted above, memory 114 may also store database 116. In some example embodiments, database 116 is a relational database. In other embodiments, database 130 may be a non-relational database, such as a key-value database, NoSQL database, a graph database, or the like. The database 116 can be used to store medical imaging data such as breast images and associated breast image data and characteristics. The medical imaging data may be stored as a plurality of medical imaging records, which may include medical imaging records for one or more patients. The medical imaging data may be stored in various formats, such as using a DICOM (Digital Imaging and Communications in Medicine) image format. The medical imaging data may be generated by radiological and other imaging procedures (e.g. ultrasound images, CT scans, MRIs X-rays etc.), and may also include markers and/or standardized codes such as codified markers defined using national/international standards (e.g. HL7, DICOM).

The archive database 140 may be communicatively coupled to the imaging server 110 and/or the workstation 120 over a network such as the internet. While the archive database 140 is shown as separate from the imaging server 110, in some embodiments the functions of the archive database 140 and imaging server 110 may be combined into a single imaging server or a distributed server. In general, the archive database 140 may include components such as a processor, memory, communication interface and database similar to processor 112, memory 114, database 116 and communication interface 118 of imaging server 110. The archive database 140 can be used to store medical image data for longer periods of time and with larger capacity than may be provided at a clinician workstation and/or an imaging server 110. The medical image data may then be retrieved from the archive database 140 as needed. In some cases, the archive database 140 and/or imaging server 110 may form part of a system for managing electronic patient record or electronic medical records, and may include medical imaging data generated from a plurality of medical sites (e.g. hospitals, clinics, imaging clinics etc.).

As used herein, the term "software application" or "application" refers to computer-executable instructions, particularly computer-executable instructions stored in a non-transitory medium, such as a non-volatile memory, and executed by a computer processor. The computer processor, when executing the instructions, may receive inputs and transmit outputs to any of a variety of input or output devices to which it is coupled.

For instance, an image viewing application 130 may be stored on the workstation 120. Although shown separately from memory 124, it will be understood that image viewing application 130 may be stored in memory 124. In general, the image viewing application 130 may provide a user of the workstation 120 with user interfaces for managing and reviewing medical image data stored in memory 124 and retrieved from imaging server 110 and/or archive database 140. While image viewing application 130 is shown as being provided on the workstation 120, the image viewing application 130 may be provided as a cloud application accessible to the workstation 120 over the Internet. The image viewing application 130 may communicate with imaging server 110 to request breast image data and receive breast image data from the server 110.

The imaging server 110, clinician device 120 and archive database 140 may have various additional components not shown in FIG. 1. For example, additional input or output devices (e.g., keyboard, pointing device, etc.) may be included beyond those shown in FIG. 1.

It should be understood that the system 100 may be implemented in hardware or software or a combination of both. Specifically, various modules of medical system 100 are preferably implemented in computer programs executing on programmable computers, each comprising at least one processor, a data storage system, at least one input device and at least one output device. Without limitation, the programmable computers may be a mainframe computer, server, personal computer, laptop, personal data assistant, cellular telephone, smartphone or tablet device.

In an exemplary implementation, aspects of the system 100 are implemented in software and installed on the hard drive of any suitable client workstation 120, such that the client workstation interoperates with an imaging server 110 in a client-server configuration. The imaging server 110 may store the database 116 and imaging records for a particular patient. The records in the database 116 may be requested by the processor 112 of the clinician workstation 120, in response to input from a user of the workstation 120. The requested image data may then be transmitted to the workstation 120 and displayed using display device 126 for review by a clinician.

Rather than transferring the entirety of each requested image to the workstation 120, medical image data may be determined for each image and then transmitted to the clinician workstation. For instance, the clinician workstation 120 may transmit to the imaging server 110 identifying characteristics of a mammography image to be retrieved.

The identifying characteristics may include a pre-determined breast window that corresponds to the mammography image to be retrieved. The pre-determined breast window can be applied to a mammography image stored in the database 116 or in archive database 140 to identify the image data for transmission. As the images stored in the database 116 and/or in archive database 140 may be unprocessed, using a pre-determined breast window determined from a different mammography image (but which corresponds to that same image, such as the same image captured at a different time period) may reduce the amount of data needed to be transmitted to the clinician workstation 120.

In some embodiments, the clinician workstation 120 may store breast image data locally in memory 124. The stored breast image data can include breast window images and remainder images received from the imaging server 110. The memory 124 may include a breast image data buffer for storing the breast image data. When a request for new breast image data is transmitted to the imaging server 110, the image viewing application 130 determines that insufficient storage space is available in the breast image data buffer. The image viewing application 130 may then identify currently-stored breast image data that can be discarded or overwritten to allow the newly request breast image data to be stored in the breast image data buffer.

The image viewing application 130 may determine a breast image priority for the breast image data currently stored in the breast image data buffer. If a clinician is currently reviewing breast image data for a particular patient, breast image data for other patients may be given lower priority. The breast image priority may be used to determine what breast image data can be discarded or overwritten.

Images more likely to be requested by a clinician at the workstation 120 can be given a higher priority. For example, breast image priority may indicate that breast window images have a greater priority than remainder images because breast window images may be more likely to include data relevant to a clinician's assessment. Additionally, breast window images that the clinician has already reviewed may be given a lower priority than breast window images stored in the buffer that the clinician has requested but not yet reviewed.

When insufficient storage capacity is identified, the image viewing application 130 may determine if any remainder images are stored in the breast image data buffer. The image viewing application may release at least one identified remainder image from memory 124 make additional storage space available. In some embodiments, the image viewing application 130 may discard breast window images from the memory 124, if and only if, no remainder images are stored in the memory 124. If breast window images are discarded from the memory 124, the breast image priorities determined for the breast window images may be used to determine which breast window images to discard.

Figure 2:
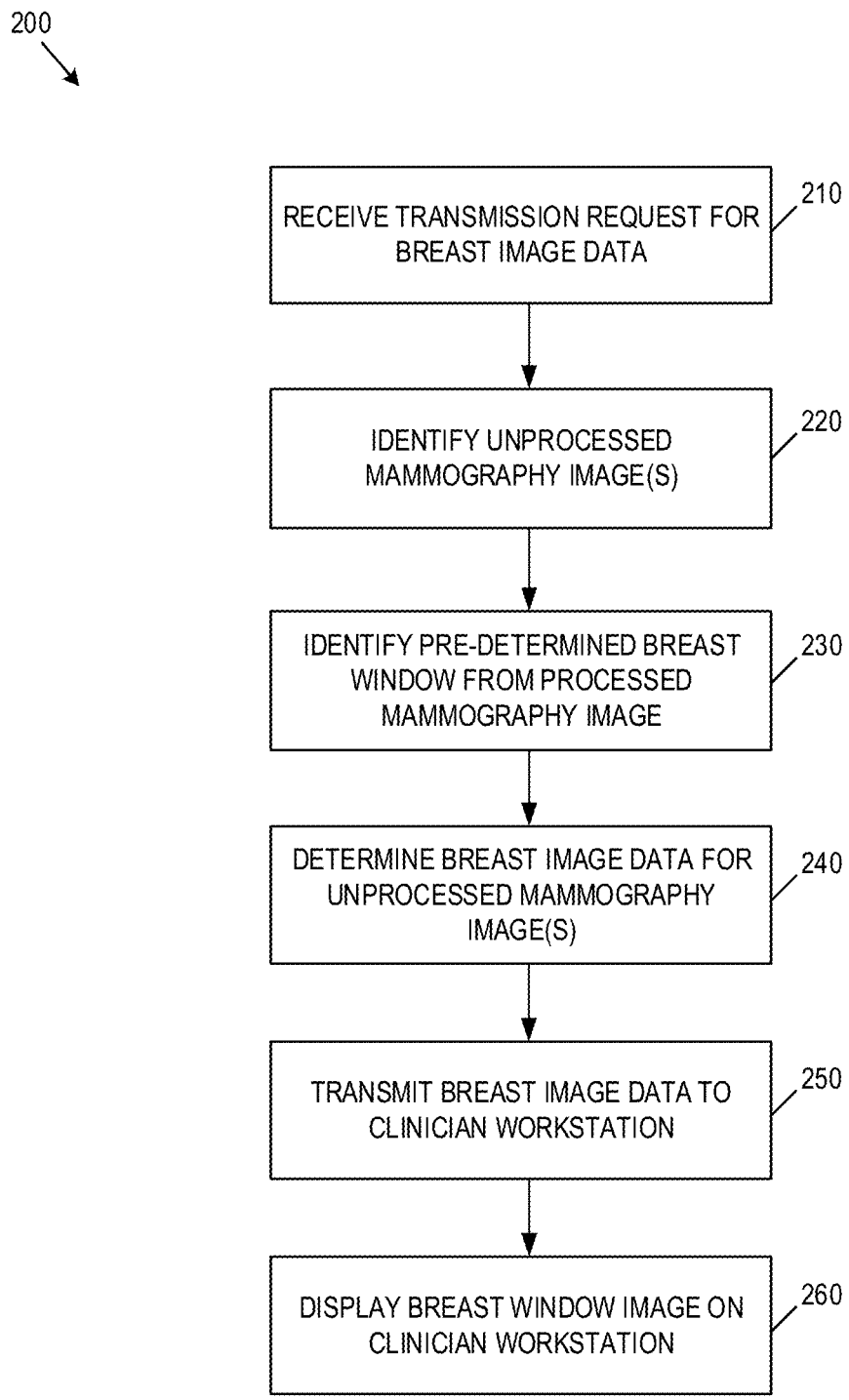
FIG. 2 is a flowchart diagram illustrating the steps of a method for providing medical imaging data within the system of FIG. 1.

Referring now to FIG. 2, shown therein is a flowchart illustrating an example method 200 for providing breast image data. Method 200 is an example of a method that may be performed by a medical imaging system such as system 100.

At 210, a transmission request for breast image data can be received at a medical imaging database (e.g. database 116) from a clinician workstation (e.g. workstation 120). The transmission request can include identifying information for a particular mammography image. For example, a current mammography image may be stored locally on the clinician workstation. The transmission request may include identifying characteristics to allow a mammography image corresponding to the current mammography image but acquired at a different time (such as a previous appointment) to be retrieved from the medical imaging database.

The identifying characteristics for the current mammography image may include patient identifying information to allow the corresponding mammography images for the same patient to be identified. The identifying characteristics can also include imaging characteristics such as breast side (left or right), imaging view (e.g. a Cranial-Caudal view or a mediolateral-oblique view), imaging modality, imaging settings etc.

The identifying characteristics may identify the one or more mammography images being requested. In some cases, the identifying characteristics may also include scaling characteristics (such as the imaging modality and imaging settings) that can be used to determine a scale factor between the stored mammography image and other corresponding mammography images. A scaling relationship between the imaging modality and imaging settings of a processed mammography image corresponding to the particular mammography image and one or more unprocessed mammography images can be determined. This scaling relationship can indicate how the stored mammography image may need to be adjusted so it has the same alignment and zoom factor as a processed mammography image.

At 220, at least one unprocessed mammography image stored by the medical imaging database that corresponds to the particular mammography image can be identified using the identifying characteristics. As used herein, the term processed mammography image generally refers to a mammography image for which a breast window has been identified. An unprocessed mammography image generally refers to a mammography image for which a breast window is not currently identified, or is not identified in a manner that allows the breast window within that mammography image to be determined.

In some cases, a plurality of unprocessed mammography images may be determined at 220. For instance, where mammography images have been captured for a patient at multiple visits (i.e. acquired at different times) and are stored in the imaging database, each of the stored unprocessed mammography images corresponding to the identifying characteristics may be identified.

At 230, a pre-determined breast window can be identified for the particular mammography image. The pre-determined breast window can be defined by processed mammography data of a processed mammography image that corresponds to the particular mammography image.

In some embodiments, a current mammography image may be stored at the clinician workstation. The processed mammography data may be generated by processing the current mammography image at the clinician workstation to identify the pre-determined breast window. As mentioned above, the processed mammography data may be generated using methods described in U.S. Pat. No. 8,649,578 and/or US Patent Application Publication No. US2015/0199790A1.

In some cases, the identifying characteristics in the transmission request from the clinician workstation may include the processed mammography data defining the pre-determined breast window. The processed mammography data may include coordinates or data sufficient to determine a breast window location within a corresponding mammography image.

In some embodiments, the pre-determined breast window may be stored at the medical imaging database in association with the identifying characteristics for the particular mammography image. This may allow the pre-determined breast window to be applied to additional mammography images stored on the database 116 or in archive database 140. This may also allow the breast window to be easily determined when subsequent mammography images are generated that correspond to the identifying characteristics.

In some embodiments, the pre-determined breast window may be determined using a processed mammography image already stored on the imaging database. For instance, a plurality of initial mammography images corresponding to the mammography image can be identified at the medical imaging database. The plurality of initial mammography images can include the at least one unprocessed mammography image as well as a processed mammography image. The processed mammography image can be identified in the plurality of initial mammography images, and the processed mammography data of that processed mammography image can be identified. This processed mammography can then be used to determine the pre-determined breast window for the particular mammography image.

At 240, for each of the at least one unprocessed mammography images, breast image data stored in the medical imaging database can be determined. The breast image data can include a breast window image determined by applying the pre-determined breast window to that unprocessed mammography image. The breast image data generally refers to image data to be transmitted from the database to the clinician workstation for review by a clinician.

In some cases, an unprocessed mammography image may be scaled prior to identifying the breast window image using the pre-determined breast window. For example, a scaling relationship can be determined between an unprocessed mammography image and the processed mammography image from which the pre-determined breast window was generated. This may allow the unprocessed mammography image to be aligned and adjusted to correspond to the processed mammography image before applying the pre-determined breast window data to the unprocessed mammography image. This scaling factor or relationship can be used to account for minor differences between images acquired at different times, such as changes in imaging modality, changes in the distance from the imaging modality to the breast, and changes in zoom factors for example.

Each of the at least one unprocessed mammography images may include a breast window region and a secondary region. The breast window region generally refers to the portion of that mammography image that includes breast tissue (and may also include margin around the breast tissue such as a rectangular window). The secondary region generally refers to the region of the unprocessed mammography image that does not include breast tissue and is otherwise outside a window around the breast tissue. The secondary region may also be referred to as a background region.

At 250, the breast image data can be transmitted from the medical imaging database to the clinician workstation. In some cases, the breast image data transmitted from the medical imaging database to the clinician workstation includes image data corresponding to the breast window region and excludes image data corresponding at least a portion of the secondary region.

That is, the breast window image for an unprocessed mammography image can be determined at the medical imaging database (e.g. server 110) by applying the pre-determined breast window. This breast window image may be extracted from the unprocessed mammography image as the breast image data. The breast image data transmitted to the clinician workstation 120 may then include the breast window image and exclude secondary regions of the unprocessed mammography image.

Figure 4A:
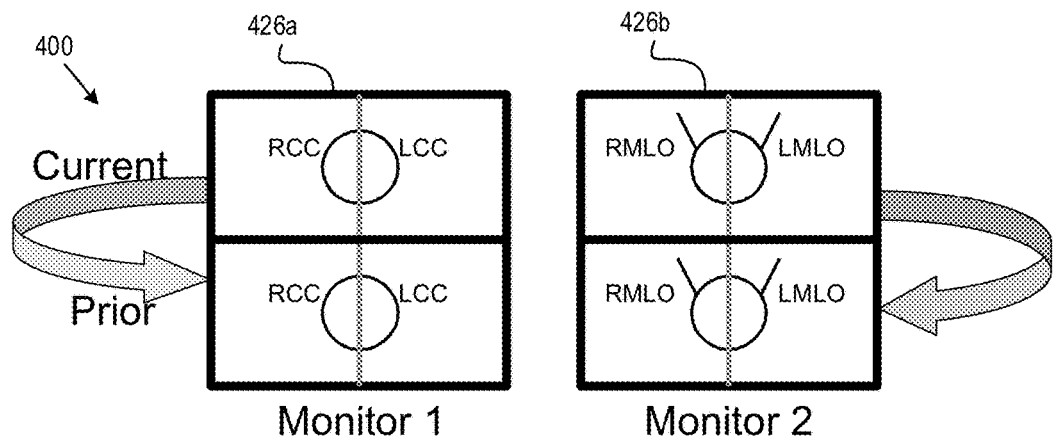
FIG. 4A is a diagram illustrating an example of medical imaging data being displayed in the system of FIG. 1 in accordance with an embodiment.
Figure 4B:
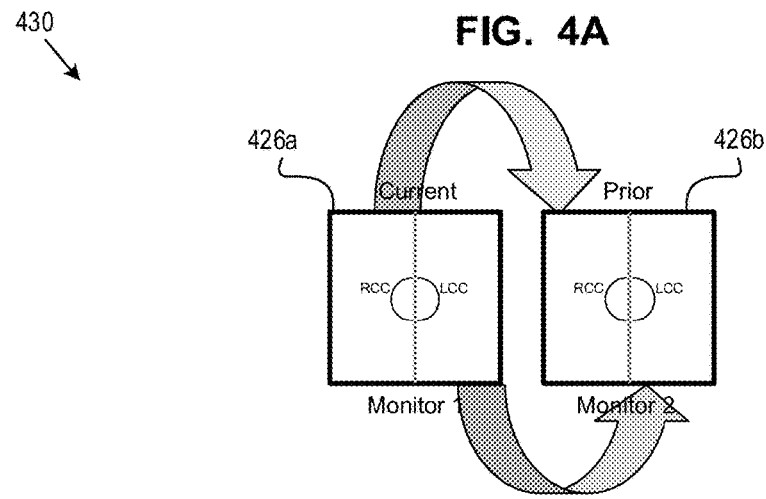
FIG. 4B is a diagram illustrating an example of medical imaging data being displayed in the system of FIG. 1 in accordance with another embodiment.
Figure 4C:
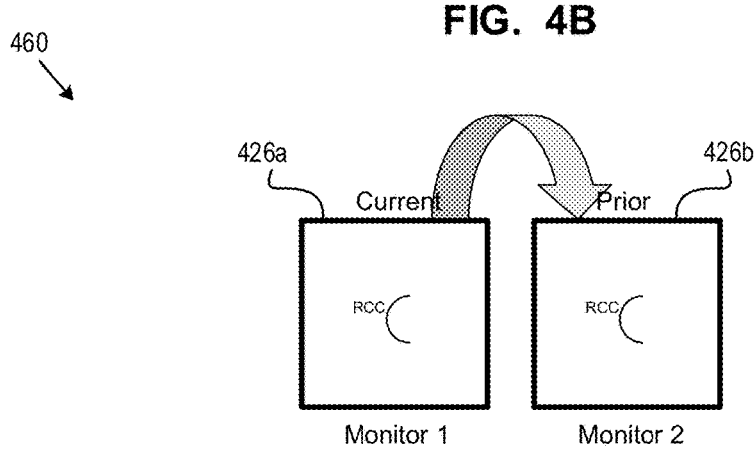
FIG. 4C is a diagram illustrating an example of medical imaging data being displayed in the system of FIG. 1 in accordance with a further embodiment.

At 260, the breast window image for the unprocessed mammography images received from the medical imaging database can be displayed at the clinician workstation using display device 126. In some cases, the breast window image for an unprocessed mammography image may be displayed concurrently with another corresponding breast window image, such as a breast window image of a current mammography image. In some cases, the display device 126 may include multiple monitors or displays to allow multiple images to be displayed concurrently to a clinician, as shown in FIGS. 4A-4C and described below.

In some embodiments, a subsequent transmission request for additional breast image data can be received at the medical imaging database from the clinician workstation. The subsequent transmission request may identify a particular unprocessed mammography image of the at least one unprocessed mammography image. Additional breast image data for the particular unprocessed mammography can then be transmitted from the medical imaging database to the clinician workstation. The additional breast image data may include an additional portion of the secondary region that was excluded from the breast image data transmitted originally.

A subsequent transmission request may be transmitted after the initial breast image data is delivered or is displayed. The subsequent transmission request may identify that the background region of the mammography image is desired to be viewed at the clinician workstation. In some cases, the additional breast image data may be transmitted from the medical imaging database in response to determining that there is sufficient network bandwidth (e.g. a system idle condition). In some cases, the subsequent transmission may occur only if there is sufficient storage capacity in the memory 124 of the workstation 120 to store background image data.

In some embodiments, the particular mammography image may belong to an image series including a plurality of related mammography images. In such embodiments, steps 220-260 may be repeated for each related image of that image series. That is, at least one unprocessed mammography image stored in the medical imaging database that corresponds to a particular related mammography image can be identified. In some cases, the identifying characteristics in the transmission request may include image series identifiers indicating that multiple corresponding mammography images from an image series are being requested.

The pre-determined breast window for a related mammography image can be identified using processed mammography data as described above. As mentioned above, the identifying characteristics included in the transmission request may include processed mammography data defining the pre-determined breast window. In some cases, the pre-determined breast window may be an overview breast window determined in accordance with the methods described in U.S. patent application Ser. No. 14/155,851, published as US2015/0199790A1. In some cases, the pre-determined breast window (either an individual breast window or overview breast window) may be determined from processed mammography data stored on the medical imaging database along with a processed mammography image that corresponds to the particular mammography image being requested.

Breast image data for the at least one unprocessed mammography image that corresponds to the particular related mammography image can be determined to include a breast window image that is determined by applying the pre-determined breast window, and the breast image data can be transmitted to the clinician workstation. The breast window image for each related image of the series can be displayed in turn at the clinician workstation as the clinician reviews the image series.

Figure 3A:
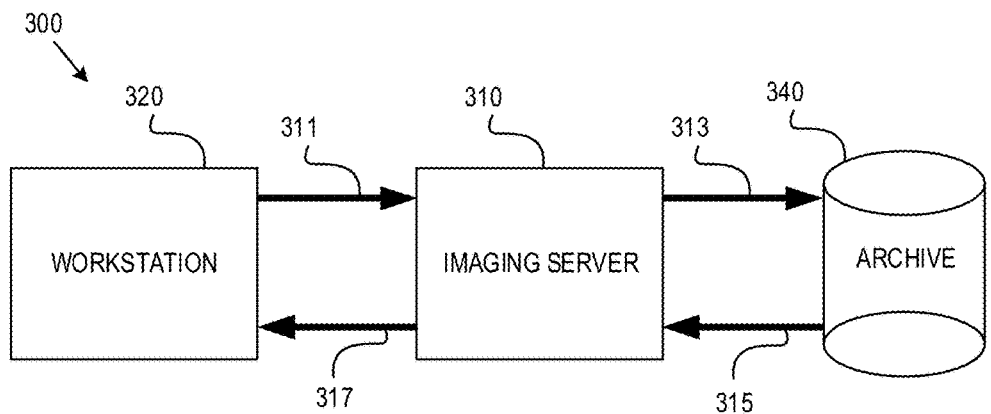
FIG. 3A is a diagram illustrating data flow in an example system for providing medical imaging data in accordance with an embodiment.

Referring now to FIG. 3A, shown therein is an example system 300 illustrating data flow between a clinician workstation 320, an imaging server 310 and an archive database 340. The server 310, workstation 320 and archive database 340 may generally correspond to the server 110, workstation 120 and archive database 140 of system 100.

As shown in system 300, a transmission request 311 may be sent from workstation 320 to imaging server 310. The transmission request 311 may include identifying characteristics for a particular mammography image (or mammography image series) a clinician using workstation 320 is interested in reviewing.

The imaging server 310 may determine, using the identifying characteristics in the transmission request, that one or more mammography images corresponding to the particular mammography image are stored at the imaging server 310. The one or more mammography images generally include at least one unprocessed mammography image.

In some cases, the imaging server 310 may determine that additional corresponding mammography images may be stored on archive database 340. In some cases, the imaging server 310 may determine that no mammography images are stored directly on that server, but that the one or more corresponding mammography images are stored on archive database 340. In either case, the imaging server 310 may transmit an archive request 313 including the identifying characteristics to the archive database 340. The archive database 340 may then transmit an archive response 315 to the imaging server 310 that includes breast image data for a corresponding mammography image.

In some cases, the mammography images stored on the imaging server 310 and/or archive database 340 may include only unprocessed mammography images. In such cases, the identifying characteristics transmitted from the workstation 320 may include processed mammography data that defines a pre-determined breast window. This pre-determined breast window can be applied to the unprocessed mammography images stored on imaging server 310 and/or archive database 340 to extract a breast window image before the breast image data is transmitted from imaging server 310 and/or archive database 340.

In some cases, a processed mammography image may be stored on the imaging server 310 and/or archive database 340 that includes processed mammography data including a pre-determined window for the particular mammography image. In such cases, this pre-determined breast window associated with the processed mammography image stored on the imaging server 310 and/or archive database 340 can be applied to other unprocessed images to extract a breast window image.

Once the breast image data for the one or more mammography images stored on the imaging server 310 and/or archive database 340 is determined, a breast image response 317 can be sent to the workstation 320. The breast image response 317 generally includes breast image data including the breast window image for each of the mammography images stored on the imaging server 310 and/or archive database 340. This breast image data can then be displayed at the workstation.

Figure 3B:
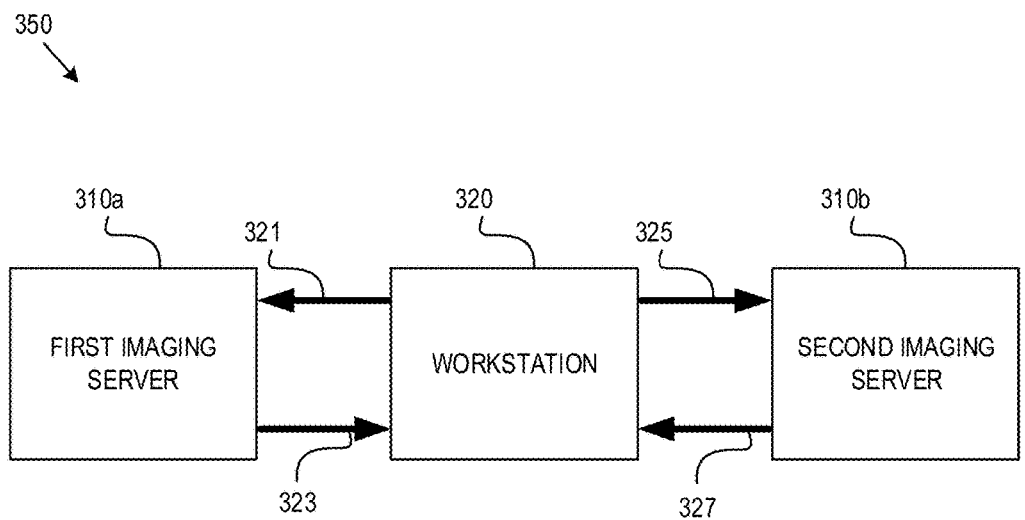
FIG. 3B is a diagram illustrating data flow in another example system for providing medical imaging data in accordance with an embodiment.

Referring now to FIG. 3B, shown therein is another example system 350 illustrating data flow between a clinician workstation 320, a first imaging server 310a and a second imaging server 310b. The data flow shown in system 350 is an example of how a pre-determined breast window may be retrieved from a first imaging database and then transmitted to a second imaging database.

An initial transmission request 321 may be sent from workstation 320 to first imaging server 310a. The initial request 321 may include identifying characteristics for a particular mammography image. The first imaging server 310a may have stored thereon a processed mammography image that corresponds to the particular mammography image. The first imaging server 310a can identify the processed mammography image using the received identifying characteristics. The first imaging server 310a may then transmit a breast window image of the processed mammography image to the workstation 320 in first response 323.

The initial transmission request 321 may also include a request for processed mammography data from the first imaging server 310a. In the first response 323, the first imaging server 310a may include the processed mammography data that defines the pre-determined breast window used to generate the breast window image. The workstation 320 can then send a second transmission request 325 to the second imaging server 310b and include the processed mammography data in the identifying characteristics. If the second imaging server 310b has stored thereon unprocessed mammography images corresponding to the particular mammography image, the processed mammography data can be used to generate breast image data including a breast window image from the unprocessed mammography images. The breast image data can then be transmitted to the workstation 320 in a second response 327 for display on a display device of the workstation 320.

Referring now to FIG. 4A, shown therein is an example diagram 400 illustrating user interfaces that may be displayed to a clinician using display device 126. As shown in FIG. 4A, the display device 126 may include a pair of monitors 426a and 426b.

The first monitor 426a is displaying two current mammography images that are right and left Cranial-Caudal views of a patient's breast. The first monitor 426a is also displaying two previous mammography images that are right and left Cranial-Caudal views of the same patient's breast acquired at a different time. The second monitor 426b is displaying two current mammography images that are right and left mediolateral-oblique views of the patient's breast. The second monitor 426b is also displaying two previous mammography images that are right and left mediolateral-oblique views of the same patient's breast acquired at the different time.

A pre-determined breast window was determined from the current mammography images and transmitted to a medical imaging database storing the previous mammography images along with identifying characteristics for the current mammography images. The medical imaging database identified the previous mammography images using the identifying characteristics, and then applied the pre-determined breast window to those mammography images to extract a breast window image. The breast window image could then be transmitted from the medical imaging database to the clinician workstation and display on monitors 426a and 426b without requiring the remainder of the images to be transmitted.

Referring now to FIGS. 4B and 4C, shown therein are additional diagrams 430 and 460 illustrating example user interfaces that may be shown using display device 126. In FIG. 4B, the first monitor 426a displays two current mammography images that are right and left Cranial-Caudal views of a patient's breast while the second monitor 426b displays two previous mammography images that are right and left Cranial-Caudal views of the same patient's breast acquired at a different time retrieved from a medical imaging database as described herein. In FIG. 4C, the first monitor 426a displays a current mammography image that is a right side Cranial-Caudal view of a patient's breast while the second monitor 426b displays a previous mammography image that is the same right side Cranial-Caudal view of the patient's breast acquired at a different time retrieved from a medical imaging database as described herein.

While the above description provides examples of the embodiments, it will be appreciated that some features and/or functions of the described embodiments are susceptible to modification without departing from the spirit and principles of operation of the described embodiments. Accordingly, what has been described above has been intended to be illustrative of the invention and non-limiting and it will be understood by persons skilled in the art that other variants and modifications may be made without departing from the scope of the invention as defined in the claims appended hereto.

The invention claimed is:

1. A method for providing breast image data, the method comprising:
  receiving from a clinician workstation, at a medical imaging database, a transmission request for breast image data, the transmission request including identifying characteristics for a particular mammography image;
  identifying at least one unprocessed mammography image stored by the medical imaging database that corresponds to the particular mammography image using the identifying characteristics;
  identifying a pre-determined breast window for the particular mammography image, the pre-determined breast window being defined by processed mammography data of a processed mammography image that corresponds to the particular mammography image;
  determining, for each of the at least one unprocessed mammography images, breast image data stored in the medical imaging database, wherein the breast image data for each unprocessed mammography image includes a breast window region and a secondary region;
  determining, for each of the at least one unprocessed mammography images, a breast window image by applying the pre-determined breast window to the breast image data stored in the medical imaging database for that unprocessed mammography image, wherein the breast window image includes the breast window region and excludes at least a portion of the secondary region for that unprocessed mammography image;
  extracting, for each of the at least one unprocessed mammography images, processed breast image data from the breast image data stored in the medical imaging database for that unprocessed mammography image, wherein the processed image data includes the breast window image determined by applying the pre-determined breast window and excludes image data corresponding to the at least a portion of the secondary region that is excluded from the breast window image;
  transmitting, for each of the at least one unprocessed mammography images, the processed breast image data extracted from the breast image data for that unprocessed mammography image from the medical imaging database to the clinician workstation; and
  displaying at the clinician workstation the breast window image for each of the at least one unprocessed mammography images received from the medical imaging database.

2. The method of claim 1 further comprising
  receiving a subsequent transmission request for additional breast image data at the medical imaging database from the clinician workstation, the subsequent transmission request identifying a particular unprocessed mammography image of the at least one unprocessed mammography image; and
  transmitting additional breast image data for the particular unprocessed mammography image from the medical imaging database to the clinician workstation, wherein the additional breast image data comprises an additional portion of the secondary region that was excluded from the breast image data previously transmitted.

3. The method of claim 1, wherein the identifying characteristics in the transmission request from the clinician workstation include the processed mammography data defining the pre-determined breast window.

4. The method of claim 3, wherein a current mammography image is stored at the clinician workstation and the method further comprises
  generating the processed mammography data by processing the current mammography image at the clinician workstation to identify the pre-determined breast window.

5. The method of claim 4, further comprising storing the pre-determined breast window at the medical imaging database in association with the identifying characteristics for the mammography image.

6. The method of claim 1, further comprising
  identifying a plurality of initial mammography images corresponding to the particular mammography image at the medical imaging database, the plurality of initial mammography images including the at least one unprocessed mammography image;
  identifying the processed mammography image in the plurality of initial mammography images; and
  identifying the processed mammography data of the processed mammography image at the medical imaging database to identify the pre-determined breast window.

7. The method of claim 1, wherein the at least one unprocessed mammography image comprises a plurality of unprocessed mammography images corresponding to the particular mammography image acquired at different times.

8. The method of claim 1, wherein the particular mammography image belongs to an image series including a plurality of related mammography images and the method further comprises, for each related mammography image of that image series:
  identifying the at least one unprocessed mammography image stored in the medical imaging database that corresponds to that related mammography image using the identifying characteristics;
  identifying the pre-determined breast window for that related mammography image, the pre-determined breast window being defined by processed mammography data of the processed mammography image that corresponds to that related mammography image;
  determining, for each of the at least one unprocessed mammography images, the breast image data stored in the medical imaging database; and transmitting, for each of the at least one unprocessed mammography images, the processed breast image data from the medical imaging database to the clinician workstation.

9. The method of claim 1, further comprising
identifying a scaling factor for a particular unprocessed mammography image, the scaling factor determined based on a scaling relationship between the particular unprocessed mammography image and the processed mammography image; and
adjusting the particular unprocessed mammography image using the scaling factor prior to applying the pre-determined breast window to the breast image data for the particular unprocessed mammography image.

10. A system for providing breast image data, the system comprising:
a medical imaging server comprising a server processor and a medical imaging database; and
a clinician workstation in communication with the medical imaging server, the clinician workstation comprising a processor, a memory and a display device;
wherein the server processor is configured to
receive a transmission request for breast image data from the clinician workstation, the transmission request including identifying characteristics for a particular mammography image;
identify at least one unprocessed mammography image stored in the medical imaging database that corresponds to the particular mammography image using the identifying characteristics;
identify a pre-determined breast window for the particular mammography image, the pre-determined breast window being defined by processed mammography data of a processed mammography image that corresponds to the particular mammography image;
determine, for each of the at least one unprocessed mammography images, breast image data stored in the medical imaging database, wherein the breast image data for each unprocessed mammography image includes a breast window region and a secondary region;
determine, for each of the at least one unprocessed mammography images, a breast window image by applying the pre-determined breast window to the breast image data stored in the medical imaging database for that unprocessed mammography image, wherein the breast window image includes the breast window region and excludes at least a portion of the secondary region for that unprocessed mammography image;
extract, for each of the at least one unprocessed mammography images, processed breast image data from the breast image data stored in the medical image database for that unprocessed mammography image, wherein the processed image data includes the breast window image determined by applying the pre-determined breast window and excludes image data corresponding to the at least a portion of the secondary region that is excluded from the breast window image; and
transmit, for each of the at least one unprocessed mammography images, the processed breast image data extracted from the breast image data for that unprocessed mammography image from the medical imaging database to the clinician workstation;
wherein the processor of the clinician workstation is configured to
receive the processed breast image data from the medical imaging database to the clinician workstation; and
display the breast window image for each of the at least one unprocessed mammography images received from the medical imaging database on the display device.

11. The system of claim 10, wherein the server processor is further configured to
receive a subsequent transmission request for additional breast image data from the clinician workstation, the subsequent transmission request identifying a particular unprocessed mammography image of the at least one unprocessed mammography image; and
transmit the additional breast image data for the particular unprocessed mammography from the medical imaging database to the clinician workstation, wherein the additional breast image data comprises an additional portion of the secondary region that was excluded from the breast image data previously transmitted.

12. The system of claim 10, wherein the identifying characteristics in the transmission request from the clinician workstation include the processed mammography data defining the pre-determined breast window.

13. The system of claim 12, wherein
the processor of the clinician workstation is further configured to
store a current mammography image in the memory of the clinician workstation; and
generate the processed mammography data by processing the current mammography image to identify the pre-determined breast window.

14. The system of claim 13, wherein the server processor is further configured to store the pre-determined breast window in the medical imaging database in association with the identifying characteristics for the particular mammography image.

15. The system of claim 10, wherein the server processor is further configured to
identify a plurality of initial mammography images corresponding to the particular mammography image on the medical imaging database, the plurality of initial mammography images including the at least one unprocessed mammography image;
identify the processed mammography image in the plurality of initial mammography images; and
identify the processed mammography data from the processed mammography image at the medical imaging database to identify the pre-determined breast window.

16. The system of claim 10, wherein the at least one unprocessed mammography image comprises a plurality of unprocessed mammography image corresponding to the particular mammography image acquired at different times.

17. The system of claim 10, wherein the particular mammography image belongs to an image series including a plurality of related mammography images and the server processor is configured to, for each related mammography image of that image series:
identify the at least one unprocessed mammography image stored in the medical imaging database that corresponds to that related mammography image using the identifying characteristics;
identify the pre-determined breast window for that related mammography image, the pre-determined breast window being defined by processed mammography data of the processed mammography image that corresponds to that related mammography image;

determine, for each of the at least one unprocessed mammography images, the breast image data stored in the medical imaging database; and transmit, for each of the at least one unprocessed mammography images, the processed breast image data from the medical imaging database to the clinician workstation.

18. The system of claim 10, wherein the server processor is further configured to identify a scaling factor for a particular unprocessed mammography image, the scaling factor determined based on a scaling relationship between the particular unprocessed mammography image and the processed mammography image; and adjust the particular unprocessed mammography image using the scaling factor prior to applying the predetermined breast window to the breast image data for the particular unprocessed mammography image.

* * * * *